United States Patent [19]

Drews et al.

[11] 4,393,841
[45] Jul. 19, 1983

[54] DEVICE FOR REGULATING THE FUEL-AIR RATIO IN INTERNAL COMBUSTION ENGINES

[75] Inventors: Ulrich Drews, Vaihingen; Peter Werner, Wiernsheim; Werner Möhrle, Stuttgart, all of Fed. Rep. of Germany

[73] Assignee: Robert Bosch GmbH, Stuttgart, Fed. Rep. of Germany

[21] Appl. No.: 276,760

[22] Filed: Jun. 24, 1981

[30] Foreign Application Priority Data

Jun. 28, 1980 [DE] Fed. Rep. of Germany ....... 3024607

[51] Int. Cl.³ .............................................. F02B 3/08
[52] U.S. Cl. .................................... 123/440; 123/489; 73/23
[58] Field of Search ................. 123/489, 440; 60/276, 60/285; 73/23

[56] References Cited

U.S. PATENT DOCUMENTS

| | | | |
|---|---|---|---|
| 3,948,228 | 4/1976 | Luchaco | 123/489 |
| 4,140,085 | 2/1979 | Rabus et al. | 123/440 |
| 4,167,163 | 9/1979 | Moder | 123/440 |
| 4,172,432 | 10/1979 | Wessel et al. | 60/276 |
| 4,208,993 | 6/1980 | Peter | 123/489 |
| 4,235,096 | 11/1980 | Yasuda et al. | 73/23 |
| 4,258,563 | 3/1981 | Yasuda et al. | 73/23 |

FOREIGN PATENT DOCUMENTS 42914 1/1982 European Pat. Off. ............ 123/440

*Primary Examiner*—Parshotam S. Lall
*Attorney, Agent, or Firm*—Edwin E. Greigg

[57] ABSTRACT

A device is proposed for regulating the fuel-air ratio in the operating mixture of an internal combustion engine and for monitoring the operational readiness of a λ sensor controlling the regulating device and functioning by the principle of ion conduction in solid electrolytes. The λ sensor has an adjustable, constant reference voltage switched opposite to it. The reference voltage approximately equals the average sensor output voltage. The level of the resultant voltage, which is established with the aid of the resultant current and has values located symmetrically with respect to the reference voltage, is monitored by comparator devices. The output signal of the comparator devices is logically processed and furnishes a signal as to the operational readiness of the sensor. In order to generate the reference voltage, a voltage divider branch having high resistance is disposed parallel to a voltage divider branch of relatively low resistance; the latter voltage divider branch further serves to establish the threshold values of the comparator devices. Because it is independent of the current draw of the comparator devices, the desired reference voltage can be adhered to very precisely, and thus the desired regulating point at which closed-loop control or regulation begins of the regulating device can also be adhered to very precisely.

5 Claims, 4 Drawing Figures

DEVICE FOR REGULATING THE FUEL-AIR RATIO IN INTERNAL COMBUSTION ENGINES

BACKGROUND OF THE INVENTION

The invention is based on a device for regulating the fuel-air ratio of the operating mixture being combusted in an internal engine using a λ sensor, which is connected with a regulating device for influencing the fuel-air ratio, and having a device for monitoring the operational readiness of the λ sensor. In order to ascertain the internal sensor resistance affecting the sensor readiness, a reference voltage is switched opposite to the sensor voltage by the interposition of a resistor. The resultant voltage ($S_r$) at the λ sensor output is capable of being monitored, by at least two comparator devices having different threshold values, as to the presence of a minimum stroke indicating the operational readiness of the λ sensor. The outputs of the comparator devices are connected with a logic processing circuit whose output signal is evaluated by an evaluation circuit as a standard for the operational readiness. This evaluation circuit generates a first signal which indicates the operational readiness and/or establishes the operation of the regulating device. A second signal indicates the non-readiness for operation of the λ sensor and/or shuts down the operation of the regulating device and switches the device over to open-loop control.

In a device of this kind (for example, U.S. Pat. No. 4,208,993), one of the comparator devices serves to ascertain whether the sensor signal is larger or smaller than an average voltage value, which, as the voltage value determining the regulating point, is located within the voltage jump of the lambda sensor output signal when λ=1. The regulating device is controlled with the output value of this comparator device. In contrast, the output values of both comparator devices taken together represent an expression of the operational readiness of the lambda sensor. This arrangement has the disadvantage, however, that the threshold values for the comparator devices and the reference voltage are picked up directly from a single voltage divider; because the comparator devices draw an electric current, this affects the magnitude of the reference voltage and thus affects the regulating point as well. Furthermore, the adjustment range of the reference voltage is limited by the location of the threshold values, and the load resistance by way of which the reference voltage is applied to the sensor output and is fixed in its value. Because of the sensitivity of the reference voltage to the withdrawal of current from the voltage divider, there are limitations placed on the possible opportunities for evaluating the resultant voltage at the lambda sensor output by means of additional evaluation devices.

OBJECT AND SUMMARY OF THE INVENTION

The device according to the invention relates to a device for regulating fuel-air ratio. A reference voltage is applied to the regulating device and is compared to a resultant voltage ($S_r$) which is generated at the sensor output. This resultant voltage is monitored by at least two comparator devices having different threshold values which are a function of the reference voltage, with respect to the presence of a minimum stroke which indicates the operational readiness of the λ sensor.

In order to establish the reference voltage, a voltage source is applied to a circuit comprising main and auxiliary voltage dividers such that the reference voltage is independent of the selection of the threshold values of the comparator devices and relatively independent of the current drawn by the same.

The outputs of the comparator devices are connected with a logic processing circuit whose output signal is evaluated by an evaluation circuit as a standard for the operational readiness. This evaluation circuit generates a first signal indicating the operational readiness and/or establishing the operation of the regulating device, and a second signal indicating the non-readiness for operation of the sensor and/or shutting down the operation of the regulating device and switching over to open-loop control.

An object of the present invention is to provide a fuel regulating device with reference voltage values which are independent of the location of the threshold values of the comparator devices and substantially independent of the withdrawal of electric current at the main voltage divider.

Another object is to provide a regulating device which compensates for initially cold lambda sensors which have high internal resistances.

The invention will be better understood and further objects and advantages thereof will become more apparent from the ensuing detailed description of two preferred embodiments taken in conjunction with the drawings.

DESCRIPTION OF THE PREFERRED EMBODIMENTS

Figure 3:
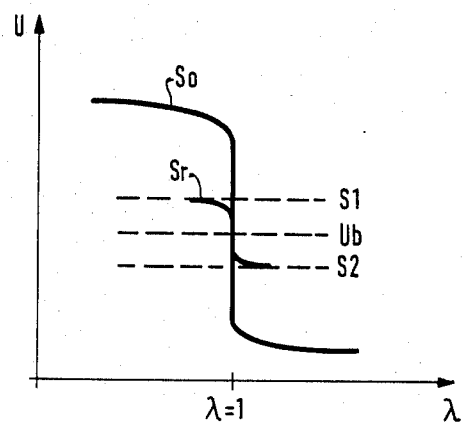
FIG. 3 is a diagram showing the sensor output signal.

The subject of the invention is a further development of the apparatus described in (U.S. Pat. No. 4,208,993). The essential component of the device according to the invention is a lambda sensor of known design, which is inserted into the exhaust system of an internal combustion engine and is subjected to the flow around it of the exhaust gases resulting from the combustion events in the cylinders of the engine. The sensor comprises a solid electrolyte, for instance zirconium dioxide, which undergoes contact on both sides. One side of the zirconium dioxide body is exposed to the exhaust gas, and the other side is exposed to a reference medium. As the result of an oxygen partial-pressure difference between the pressures at the two surfaces of the solid electrolyte body, a difference in potential is produced at the contact points, the value of which is shown in FIG. 3 for various fuel-air ratios λ. The output voltage of the lambda sensor varies abruptly at an air number λ=1. At air numbers of λ<1, the output voltage assumes values at the lambda sensor of 750–900 millivolt, given the condition that the λ sensor is in the operationally warm state. At air numbers of $\lambda>1$, the output voltage amounts to ca. 100 millivolt.

However, the $\lambda$ sensor has the disadvantage that in the cold state, the internal resistance of the sensor is extremely high, so that it is not possible to attain a voltage signal at the output of the $\lambda$ sensor which is capable of being evaluated for purposes of regulation; in particular, it is not possible to attain a clearly-defined voltage jump.

Figure 1:
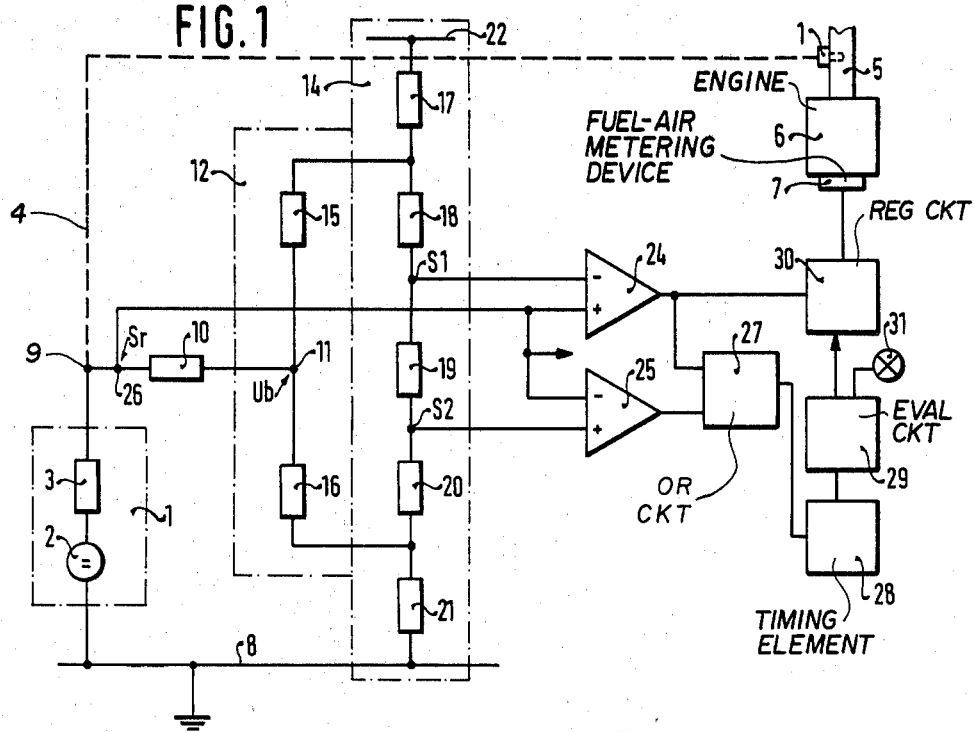
FIG. 1 shows a first exemplary embodiment of the invention, having a voltage divider for generating the reference voltage which is parallel to the main voltage divider.

In FIG. 1, the $\lambda$ sensor 1 is shown in the form of a substitute circuit diagram comprising a voltage source (original voltage) 2 and the internal resistor 3. The connection 4 represented by broken lines indicates that the $\lambda$ sensor 1 is inserted into the exhaust system 5 of an internal combustion engine 6, which is shown here only schematically. The engine is supplied by means of a fual-air metering device 7 with an operating mixture of air and fuel, which reaches the combustion chambers of the engine and is combusted there. The ratio of fuel to air may be established in a controlled manner in the fuel-air metering device and may additionally be corrected by means of the apparatus shown in FIG. 1.

In the interest of making the exhaust gases free of toxic substances, the intention is that the superimposing regulating device for the fuel or air metering be activated as soon as possible after the engine has been put into operation. In order to recognize when a sensor signal has appeared which can be evaluated by the regulating device with sufficient reliability, U.S. Pat. No. 4,208,993 proposes a circuit with which a sensor output voltage, which varies with the magnitude of the internal resistance, is picked up with the aid of threshold switches. After the fixed threshold values are exceeded, a signal is generated which causes the regulation to begin. FIG. 1 shows the essential features of this circuit.

One output of the $\lambda$ sensor 1 is connected with the ground line 8 of the voltage supply device, while the other output 26 is connected via a resistor 10 with the middle pickup 11 of a voltage divider 12 comprising the resistors 15 and 16. This voltage divider branches off from a main voltage divider 14, which has resistors 17, 18, 19, 20 and 21 disposed in series and is located between the positive supply line 22 and the ground line 8. The voltage divider 12 is located parallel to the middle resistors 18, 19 and 20 of the main voltage divider 14. The main voltage divider is supplied from a constant voltage source or a constant current source.

Between the middle resistor 19 and the adjacent resistor 18 of the main voltage divider 14, there is a voltage pickup $S_1$, which is connected with the inverting input of a first comparator device 24 represented in the exemplary embodiment as an operational amplifier shown in simplified form. Between the middle resistor 19 and the adjacent resistor 20 of the main voltage divider 14, there is a voltage pickup $S_2$, which is connected with the non-inverting input of a second comparator device 25, also realized here as an operational amplifier. The voltage pickups $S_1$ and $S_2$ provide the threshold voltages for the comparator devices 24 and 25 already mentioned. The non-inverting input of the first comparator device 24 and the inverting input of the second comparator device 25 are connected in common with the output 26 of the $\lambda$ sensor 1.

The outputs of the first comparator device 24 and the second comparator device 25 lead to a logic processing circuit 27, whose output is carried via a timing element 28 to an evaluation circuit 29. The output of the evaluation circuit acts upon a regulating circuit 30 and may additionally control a warning device 31. The output of the first comparator device is further connected directly with the regulating circuit 30, which emits a control signal for the fuel-air metering device 7.

The device described above functions as follows:

At the middle pickup 11 of the voltage divider 12, a constant reference voltage $U_b$ is available for use; it has the same polarity as the sensor voltage. The reference voltage is applied via the resistor 10 to the sensor output 26 and is thus opposite to the voltage source 2. At the sensor output 26, then, a voltage $S_r$ is produced, which is the result of the two voltages. As long as there is no current flowing between the $\lambda$ sensor and the reference voltage point, this voltage $S_r$ assumes the value of the reference voltage $U_b$. When there is a deviation in the sensor output voltage, either a current flows over the resistor 10 and the internal resistor 3 into the sensor, or such a current flows outward from the sensor. At the sensor output 26, a voltage $S_r$ is produced, which is between the reference voltage value and the maximum voltage source 2 or the minimum voltage source 2. This voltage $S_r$ is dependent on the internal resistance of the $\lambda$ sensor, which greatly affects the flow of current through the $\lambda$ sensor.

As a result of the opposite switching of the reference voltage $U_b$ via the constant resistor 10, it is attained that as the internal resistance at 3 decreases, voltage values can be picked up at the sensor output 26 which deviate to an increasing extend from the reference voltage as the sensor temperature increases. The upper and lower values may be disposed symmetrically with respect to the reference voltage. Beyond a certain deviation $|\Delta U| = |S_r - U_b|$, which may amount by way of example to 25 millivolt, the sensor output signal may be considered to be capable of evaluation for a subsequent regulation means. The internal sensor resistance at 3 is then low enough that the sensor signal may be evaluated without error by a subsequent comparator device for purposes of regulation.

The specific deviations $\Delta U$ from the reference voltage $U_b$ mentioned above are fixed by the threshold values $S_1$ and $S_2$ of the voltage divider 14. The internal resistance of the sensor at 3, at which the regulating circuit switches on, is also fixed by the resistance value of resistor 10. The first comparator device 24 and the second comparator device 25 serve to generate a logically evaluatable signal on the basis of the voltage present at the sensor output 26. If the voltage at the sensor output 26 exceeds the threshold value $S_1$, then the first comparator device 24 emits a logic 1 signal, and the second comparator device emits a logic 0 signal. If instead the voltage at the sensor output 26 is lower than the threshold value $S_2$, then the output of the first comparator device is logic 0 and the output of the second comparator device is logic 1. These output signals are delivered to the logic processing circuit 27, which is shown in FIG. 4 in further detail.

Figure 4:
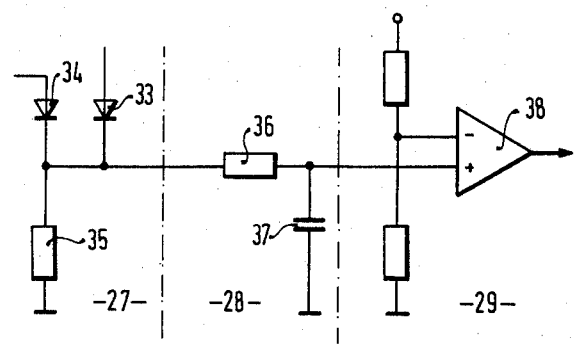
FIG. 4 shows one realization of the evaluation circuit.

FIG. 4 also includes the timing element 28 and the evaluation circuit 29.

The graph in FIG. 3 clearly explains the mode of operation of the above-described monitoring device. The voltage is indicated by the symbol $S_O$. As described, this voltage $S_O$ assumes a high value at lambda values of $\lambda<1$, drops abruptly at $\lambda=1$, and has a low voltage value at lambda values of $\lambda>1$. The resultant voltage appearing at the sensor output when the $\lambda$ sensor is cold is indicated by the symbol $S_r$. For the illustrated state of the $\lambda$ sensor, this voltage $S_r$ is below the threshold value $S_1$ or above the threshold value $S_2$, respectively.

At the output of the first comparator device 24 and at the output of the second comparator device 25, logic signals thus appear in accordance with the following table:

| Sensor | $S_O$ | 1st Op. Amp. (24) | 2nd Op. Amp. (25) |
|---|---|---|---|
| cold | $S_O \geq U_b$ | 0 | 0 |
| cold | $S_O < U_b$ | 0 | 0 |
| warm | $S_O > U_b$ | 1 | 0 |
| warm | $S_O < U_b$ | 0 | 1 |

The values for the cold sensor at the output of the operational amplifier also apply in the case where the connection between the lambda sensor and the sensor terminal 9 has been broken.

From the table, it can be seen that at a 0 signal at the outputs of the first and second comparator device, the λ sensor is not operationally ready, and that when the outputs are different from one another the lambda sensor is operationally ready. The output signals are evaluated, according to the circuitry of FIG. 4, that is, by means of an OR circuit. The first diode 33 of the OR circuit is connected to the output of the first comparator device 24, while the second diode 34 of the OR circuit is connected to the output of the second comparator device 25. The cathodes of both diodes are connected via a resistor 35, to ground and via a resistor 36, to a capacitor 37, which on the other side is likewise connected to ground. When the lambda sensor is in an operationally ready state, the timing element comprising the resistor 36 and the capacitor 37 is subjected, via the above-described circuit, in alternation via diodes 33 and 34 respectively to a 1 signal. As a result, the capacitor can charge via the resistor 36, or if it is in a charged state, then it remains in the charged state. If no 1 signal appears at one of the operational amplifiers, then the capacitor can discharge via the resistors 36 and 35, with the capacitance and the resistance values determining the discharging time.

The evaluation device 29 comprises a comparator 38, at one input of which a reference voltage value is applied and at the other entrance of which the capacitor voltage is present. With the aid of the reference value, a specific portion of the discharging time of the timing element may be established as a delay period; after this delay period has elapsed subsequent to the most recent appearance of a 1 signal at one of the two diodes 33 or 34, the comparator 38 switches over and generates a control signal, which engages the regulating circuit 30 in a suitable manner and/or triggers the warning device 31. With this switchover of the comparator, the regulating device is rendered inactive, and the operating mixture supplied to the engine by the fuel-air metering device 7 is now controlled only in open-loop fashion.

Because a separate, second voltage divider 12 is provided for generating the reference voltage $U_b$ in addition to the main voltage divider 14, a retroactive influence by the input currents of the two comparator devices 24 and 25 upon the reference voltage $U_b$ can be prevented. The resistance is dimensioned such that the resistor 10 between the sensor output 26 and the second voltage divider 12 has substantially greater resistance than do the resistors 15 and 16 of the second voltage divider 12. Furthermore, the resistors 15 and 16 of the second voltage divider 12 have a substantially greater resistance than do the resistors 18, 19 and 20 of the main voltage divider. The desired success, that is, a relatively stable reference voltage, is attained as a result of this dimensioning. This arrangement has the further advantage that the location of the reference voltage is finally independent of the threshold values $S_1$ and $S_2$; that is, the reference voltage $U_b$ may also lie above or below these potentials.

Figure 2:
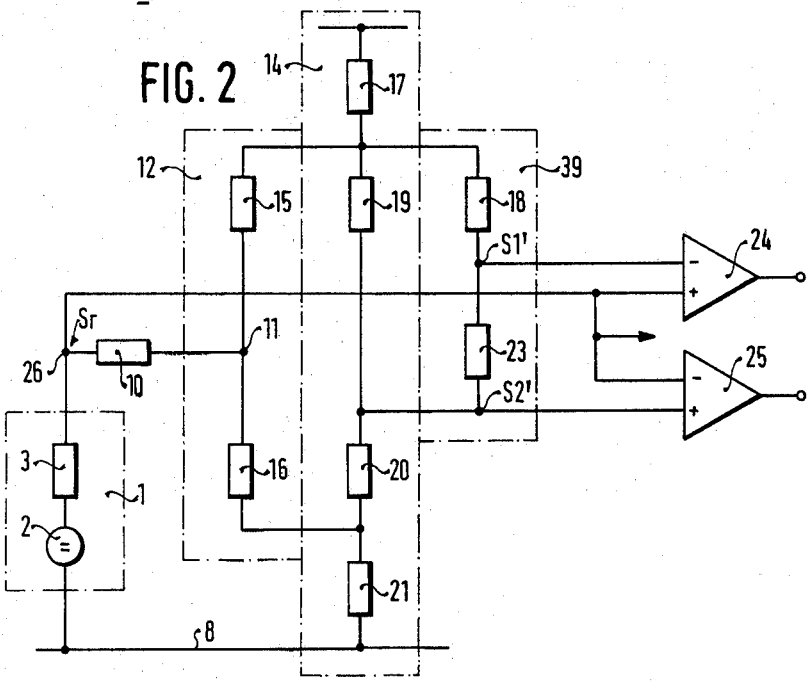
FIG. 2 shows a second exemplary embodiment, having a main voltage divider and two parallel voltage dividers for separately generating the reference voltage and the threshold values, respectively, of the comparator devices.

A further embodiment may be found in FIG. 2. Its structure is essentially the same as that of FIG. 1, and for this reason the devices switched subsequent to the comparator devices have been omitted from FIG. 2. As in the circuit according to FIG. 1, a λ sensor is provided here as well, and a reference voltage $U_b$ picked up at point 11 of the voltage divider 12 is switched opposite to the sensor voltage via the resistor 10. In the same manner as described for the preceding example, a resultant voltage $S_r$ is picked up at the sensor output 26 and evaluated by the subsequent comparator devices 24 and 25. Departing from the first exemplary embodiment, the main voltage divider in this case comprises only the resistors 17, 19, 20 and 21, which are switched in series. The second voltage divider 12 leads from the connecting point between the resistor 17 and 19 to the connecting point between the resistors 20 and 21. A third voltage divider 39 also branches off from the main voltage divider 14; it has resistors 18 and 23 switched in series and is disposed in parallel with the resistor 19 of the main voltage divider 14. The threshold value for the first comparator device 24 is picked up at pickup point $S_{1'}$ between the resistors 18 and 23 of the third voltage divider, while the threshold value for the non-inverting input of the second comparator device 25 is picked up at the pickup point $S_{2'}$ at the end of the second voltage divider 39—that is, between the resistors 19 and 20 of the main voltage divider 14'. As in the first exemplary embodiment, the resistor 10 is here again substantially larger in its resistance value than are the resistors of the second voltage divider 12. Furthermore, both the resistors of the second voltage divider 12 and the resistors of the third voltage divider 39 are substantially larger than in the case of the main voltage divider element which is parallel to them, that is, resistors 19 and 20.

The foregoing relates to preferred exemplary embodiments of the invention, it being understood that other embodiments and variants thereof are possible within the spirit and scope of the invention, the latter being defined by the appended claims.

What is claimed and desired to be secured by Letters Patent of the United States is:

1. A system for regulating the fuel-air mixture ratio being combusted in an internal combustion engine, the system having
   a lambda sensor having an internal resistance;
   a regulating device connected to the internal combustion engine to regulate the fuel-air ratio;
   a regulating circuit for controlling said regulating device;
   a monitoring circuit connected to said lambda sensor for generating a signal indicating lambda sensor readiness as a function of said internal resistance; said monitoring circuit including:
   a resistor connected at a first end to said lambda sensor and connected at a second end to said monitoring circuit for generating a resultant voltage at the first end of said resistor;
   two comparator devices having different threshold values which are connected to said lambda sensor to receive said resultant voltage and to compare said resultant voltage to said respective threshold values and to thereby generate respective output signals indicative of said comparison;

a logic processing circuit connected to receive said outputs of said two comparator devices for producing an output;

an evaluation circuit connected to receive said logic processing circuit output and connected to said regulating circuit for generating a lambda sensor readiness signal to operate said regulating device and a lambda sensor non-readiness signal to shut off said regulating device whereby said system is switched to open-loop control according to said logic processing circuit output, said system further including:

a voltage source connected to said monitoring circuit;

a first voltage divider connected across said voltage source;

a second voltage divider, connected parallel to said first voltage divider and having a pickup-point; and wherein said resistor has a high resistance value and connects said pickup-point with said lambda sensor.

2. A system as defined in claim 1, wherein said two comparator devices are connected to said first voltage divider, whereby said threshold values are determined by said first voltage divider.

3. A system as defined in claim 1, wherein said first voltage divider and second voltage divider each comprise a plurality of resistors having respective resistance values; wherein the resistance values of said first voltage divider resistors are substantially lower than the resistance values of said second voltage divider resistors.

4. A system as defined in claim 1, the monitoring circuit further including:

a third voltage divider, connected as an independent voltage source parallel to a portion of said first voltage source; wherein said two comparator devices are connected to said third voltage divider, whereby said threshold values are determined by said third voltage divider.

5. A system as defined in claim 4, wherein said first voltage divider, second voltage divider and third voltage divider each comprise a plurality of resistors having respective resistance values, and wherein the resistance values of said resistor is substantially greater than the resistance values of said second voltage divider the resistance values of said second voltage divider resistors are substantially greater than the resistance values of said first voltage divider resistors; and the resistance values of said third voltage divider resistors are substantially greater than the resistance values of said first voltage divider resistors.

* * * * *